(12) United States Patent
Sanchez et al.

(10) Patent No.: US 6,860,877 B1
(45) Date of Patent: Mar. 1, 2005

(54) HEART STABILIZER SUPPORT ARM

(75) Inventors: Dan Sanchez, Santa Barbara, CA (US); Edward R. Snow, Santa Barbara, CA (US); Ken Grace, Knoxville, TN (US)

(73) Assignee: Computer Motion, Inc., Sunnyvale, CA (US)

( * ) Notice: Subject to any disclaimer, the term of this patent is extended or adjusted under 35 U.S.C. 154(b) by 0 days.

(21) Appl. No.: 09/675,824

(22) Filed: Sep. 29, 2000

(51) Int. Cl.$^7$ ............................. A61B 17/00; A61B 1/32
(52) U.S. Cl. .......................... 606/1; 600/229; 600/234; 600/235
(58) Field of Search ............................. 606/1; 600/229, 600/227, 228, 235, 209, 210, 232, 231, 234

(56) References Cited

U.S. PATENT DOCUMENTS

| | | | |
|---|---|---|---|
| 2,466,909 A | * | 4/1949 | Periman ...................... 24/456 |
| 2,482,625 A | * | 9/1949 | Kunkel ........................ 24/523 |
| 3,497,668 A | | 2/1970 | Hirsch |
| 4,431,329 A | * | 2/1984 | Baitelle .................... 248/276.1 |
| 4,467,791 A | * | 8/1984 | Cabrera et al. ............. 600/234 |
| 4,617,916 A | * | 10/1986 | LeVahn et al. ............. 600/228 |
| 4,655,673 A | | 4/1987 | Hawkes |
| 4,819,978 A | | 4/1989 | Scheinman et al. |
| 4,867,404 A | * | 9/1989 | Harrington et al. ........... 606/46 |
| 5,078,140 A | | 1/1992 | Kwoh |
| 5,193,963 A | | 3/1993 | McAffee et al. |
| 5,217,003 A | | 6/1993 | Wilk |
| 5,222,499 A | | 6/1993 | Allen et al. |
| 5,305,203 A | | 4/1994 | Raab |
| 5,308,357 A | * | 5/1994 | Lichtman ................... 606/205 |
| 5,381,989 A | * | 1/1995 | Jackson ....................... 24/509 |
| 5,397,323 A | | 3/1995 | Taylor et al. |
| 5,402,801 A | | 4/1995 | Taylor |
| 5,410,944 A | | 5/1995 | Cushman |
| 5,417,210 A | | 5/1995 | Funda et al. |

(List continued on next page.)

FOREIGN PATENT DOCUMENTS

| | | |
|---|---|---|
| WO | WO 95/01757 | 1/1995 |
| WO | WO 99/09892 | 3/1999 |
| WO | WO 99/50721 | 10/1999 |

OTHER PUBLICATIONS

Adachi, Y., "Touch and trace on the free–form surface of virtual object," IEEE Research& Development Center, Suzuki Motor Corp., Japan, (Jan. 1993) pp. 162–168.

Alexander, III Impacts of telemation on modern society, Intl. Centre for Mechnical Sciences, 1st CISM–IFToMM Symposium, on Theory and Practice of Robots and Manipulators, (Sep. 5–8, 1973) vol. II, pp. 1122–1136.

Iwata, H., "Pen–based haptic virtual environment," IEEE Institute of Engineering Mechanics, U. of Tsukuba, Japan, (1993) pp. 287–292.

(List continued on next page.)

*Primary Examiner*—William C. Doerrler
(74) *Attorney, Agent, or Firm*—Townsend and Townsend and Crew LLP

(57) ABSTRACT

A support arm for a heart stabilizer that can be used to stabilize a heart during a beating heart coronary artery bypass graft procedure. The support arm may have an arm that is coupled to a table mount and an end effector. The table mount is adapted to be mounted to the rail of a surgical table. The end effector is adapted to hold the heart stabilizer. The arm may be adjustable to allow an end user to adjust the position of the end effector.

23 Claims, 3 Drawing Sheets

U.S. PATENT DOCUMENTS

| | | | |
|---|---|---|---|
| 5,423,648 A | 6/1995 | Akeel et al. | |
| 5,458,574 A | 10/1995 | Machold et al. | |
| 5,572,999 A | 11/1996 | Funda et al. | |
| 5,613,937 A | 3/1997 | Garrison et al. | |
| 5,631,973 A | 5/1997 | Green | |
| 5,649,956 A | 7/1997 | Jensen et al. | |
| 5,676,673 A | 10/1997 | Ferre et al. | |
| 5,681,325 A | 10/1997 | Hasson | |
| 5,695,500 A | 12/1997 | Taylor et al. | |
| 5,697,939 A | 12/1997 | Kubota et al. | |
| 5,704,900 A * | 1/1998 | Dobrovolny et al. | 600/229 |
| 5,738,649 A | 4/1998 | Macoviak | |
| 5,743,884 A | 4/1998 | Hasson | |
| 5,749,892 A | 5/1998 | Vierra et al. | |
| 5,762,458 A | 6/1998 | Wang et al. | |
| 5,784,542 A | 7/1998 | Ohm et al. | |
| 5,791,908 A | 8/1998 | Gillio | |
| 5,792,135 A | 8/1998 | Madhani et al. | |
| 5,797,900 A | 8/1998 | Madhani et al. | |
| 5,807,243 A | 9/1998 | Vierra et al. | |
| 5,808,665 A | 9/1998 | Green | |
| 5,855,583 A | 1/1999 | Wang et al. | |
| 5,876,325 A | 3/1999 | Mizuno et al. | |
| 5,888,190 A * | 3/1999 | Meyer et al. | 600/102 |
| 5,894,843 A | 4/1999 | Benetti et al. | |
| 5,923,770 A | 7/1999 | O'Donnell et al. | |
| 5,931,832 A | 8/1999 | Jensen | |
| 5,971,976 A | 10/1999 | Wang et al. | |
| 6,021,694 A * | 2/2000 | Beger | 73/862.21 |
| 6,036,641 A * | 3/2000 | Taylor et al. | 600/231 |
| 6,056,282 A * | 5/2000 | Desmarais | 269/152 |
| 6,102,854 A * | 8/2000 | Cartier et al. | 600/228 |
| 6,113,534 A * | 9/2000 | Koros et al. | 600/213 |
| 6,149,583 A | 11/2000 | Vierra et al. | |
| 6,210,323 B1 | 4/2001 | Gilhuly et al. | |
| 6,290,644 B1 * | 9/2001 | Green et al. | 600/235 |
| 6,306,146 B1 * | 10/2001 | Dinkler | 606/130 |
| 6,315,718 B1 * | 11/2001 | Sharratt | 600/228 |
| 6,331,157 B2 * | 12/2001 | Hancock | 600/232 |
| 6,371,906 B1 * | 4/2002 | Borst et al. | 600/37 |
| 6,398,726 B1 | 6/2002 | Ramans et al. | |
| 2002/0014567 A1 * | 2/2002 | King et al. | 248/276.1 |
| 2002/0045888 A1 * | 4/2002 | Ramans et al. | 606/1 |

OTHER PUBLICATIONS

Mack, et al., "Video–assisted coronary bypass grafting on the beating heart," Ann. Thorac. Surg., (1997) 63:S100–103.

Madhani, A., "Thesis Proposal: Force–Reflecting Teleoperated Endoscopic Surgery," MIT Department of Mechanical Engineering and Artificial Intelligence Laboratory, Cambridge, MA, (Nov. 17, 1995) pp. 1–6 w/attachments pp. 1–2.

Rovetta et al., "The first experiment in the world of robotic telesurgery for laparoscopy carried out by means of satellites network and optical fibres networks on (Jul. 7, 1993)," IEEE Telerobotics Laboratory, Italy, Institute of Clinical Surgery, Italy, Jet Propulsion Laboratory, Pasadena, USA, pp. 51–56.

Sukthankar et al., "Towards force feedback in laparoscopic surgical tools," IEEE, Human Interface Laboratory Dept. of Biomedical Engineering, Ohio, (1994) pp. 1041–1042.

* cited by examiner

HEART STABILIZER SUPPORT ARM

BACKGROUND OF THE INVENTION

1. Field of the Invention

The present invention relates to a support arm for a heart stabilizer used during a coronary surgical procedure.

2. Background Information

Coronary artery disease can lead to insufficient blood flow that can cause angina and ischemia. A coronary artery bypass graft (CABG) surgical procedure is sometimes required to correct this condition. In a CABG procedure an incision is made in the artery adjacent to the diseased area. The internal mammary artery of the patient is then severed and attached to the artery at the point of JP incision.

It is generally difficult to perform a CABG procedure with a beating heart. One solution is to stop the heart and connect the patient to a cardiopulmonary bypass system that supplies oxygen to the brain. Connecting the patient to the cardiopulmonary bypass system increasing the time required to perform the procedure and decreases the likelihood of success. Additionally, the heart must be successfully resuscitated.

There have been developed procedures to perform "beating heart" CABG procedures that do not require a cardiopulmonary bypass system. A heart stabilizer is typically utilized in a beating heart "CABG" to minimize the movement of the heart at the surgical site. Heart stabilizers typically include an end effector located at the end of an articulate arm. The end effector pushes down on the heart area adjacent to where the surgeon grafts the artery.

Historically CABG procedures are performed in an "open" chest cavity where the sternum is cut open. There have also been developed minimally invasive CABG procedures that are performed with the assistance of a robotic system. Such a robotic system is sold by Computer Motion, Inc. of Goleta, Calif. under the trademark ZEUS and is disclosed in U.S. Pat. No. 5,762,458. The ZEUS system can be utilized to perform minimally invasive beating heart CABG procedures. Minimally invasive beating heart CABG procedures require a heart stabilizer that can be inserted into a patient through a port. The heart stabilizer is typically held by a surgeon's assistant. The assistant may have to hold the stabilizer in position for a relatively long period of time. This may lead to fatigue. It is desirable to provide a mechanism which can support the heart stabilizer so that a surgical aide does not have to hold the stabilizer.

BRIEF SUMMARY OF THE INVENTION

One embodiment of the present invention is a support arm for a heart stabilizer. The support arm may have an arm that is coupled to a table mount and an end effector.

DETAILED DESCRIPTION OF THE PREFERRED EMBODIMENT

In general the present invention includes a support arm that can be mounted to a surgical table and support a heart stabilizer. The heart stabilizer can be inserted into a patient and utilized to perform a beating heart coronary artery bypass graft (CABG) procedure. The support arm may be adjustable to allow an end user to accurately position the end effector of the arm.

Figure 1:
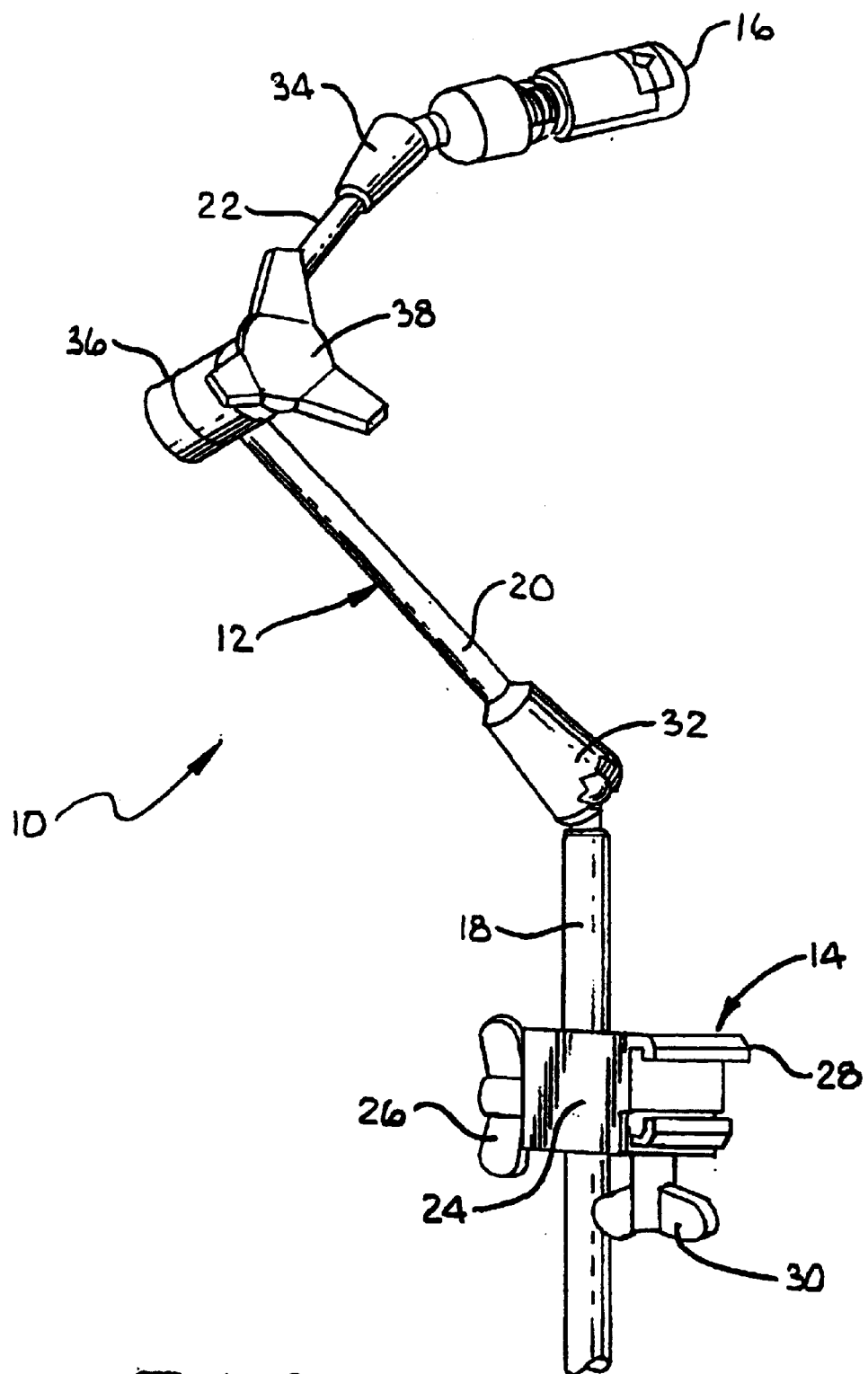
FIG. 1 is a perspective view of an embodiment of a support arm of the present invention.

Referring to the drawings more particularly by reference numbers, FIG. 1 shows an embodiment of a support arm 10 of the present invention. The support arm 10 includes an arm 12 that is coupled to a table mount 14. The table mount 14 is adapted to be secured to a surgical table (not shown). The support arm 10 further includes an end effector 16 that is coupled to the arm 12. The end effector 16 is adapted to hold a surgical instrument such as a heart stabilizer (not shown). The support arm 10 provide an apparatus that can support a heart stabilizer during a surgical procedure. It is desirable to provide a support arm 10 to hold the heart stabilizer so that a surgical aide does not have to hold the stabilizer throughout the procedure, particularly a CABG procedure which may require hours to perform.

The arm 12 may include a first linkage 18 that is coupled to the table mount 14 and a second linkage 20 coupled to the first linkage 18. The arm 12 may further have a third linkage 22 coupled to the second linkage 20.

The first linkage 18 may extend through a clearance hole (not shown) in a base 24 of the table mount 16. The table mount 14 may have an arm clamp 26 that can be rotated to engage the first linkage 18 and secure the position of the end effector 16 in a vertical direction. The arm clamp 26 can be rotated in an opposite direction to disengage the clamp 26 and allow an end user to move the first linkage 18 and adjust the height of the end effector 16.

The table mount base 24 may include a jaw section 28 that can clasp onto the rail of an operating table (not shown). The jaw section 28 can be secured to the table rail by a table clamp 30.

The second linkage 20 may be coupled to the first linkage 18 by a first ball joint 32. Likewise, the end effector 16 may be coupled to the third linkage 22 by a second ball joint 34. The third linkage 22 may be coupled to the second linkage 20 by a pivot joint 36. The ball joints 32 and 34, and pivot joint 36 provide the support arm six degrees of freedom. The position of the arm 12 and end effector 16 can be secured and locked in place by rotating a locking knob 38. The locking knob 38 clamps the pivot joint 36 to prevent relative movement between the third 22 and second 20 linkages. Rotation of the locking knob 38 also moves corresponding wedges (not shown) into fib the ball joints 32 and 34 to secure and lock the second linkage 20 and the end effector 16, respectively. The arm 12 and table mount 16 can be purchased from KARL STORZ under part number 28172H.

Figure 2:
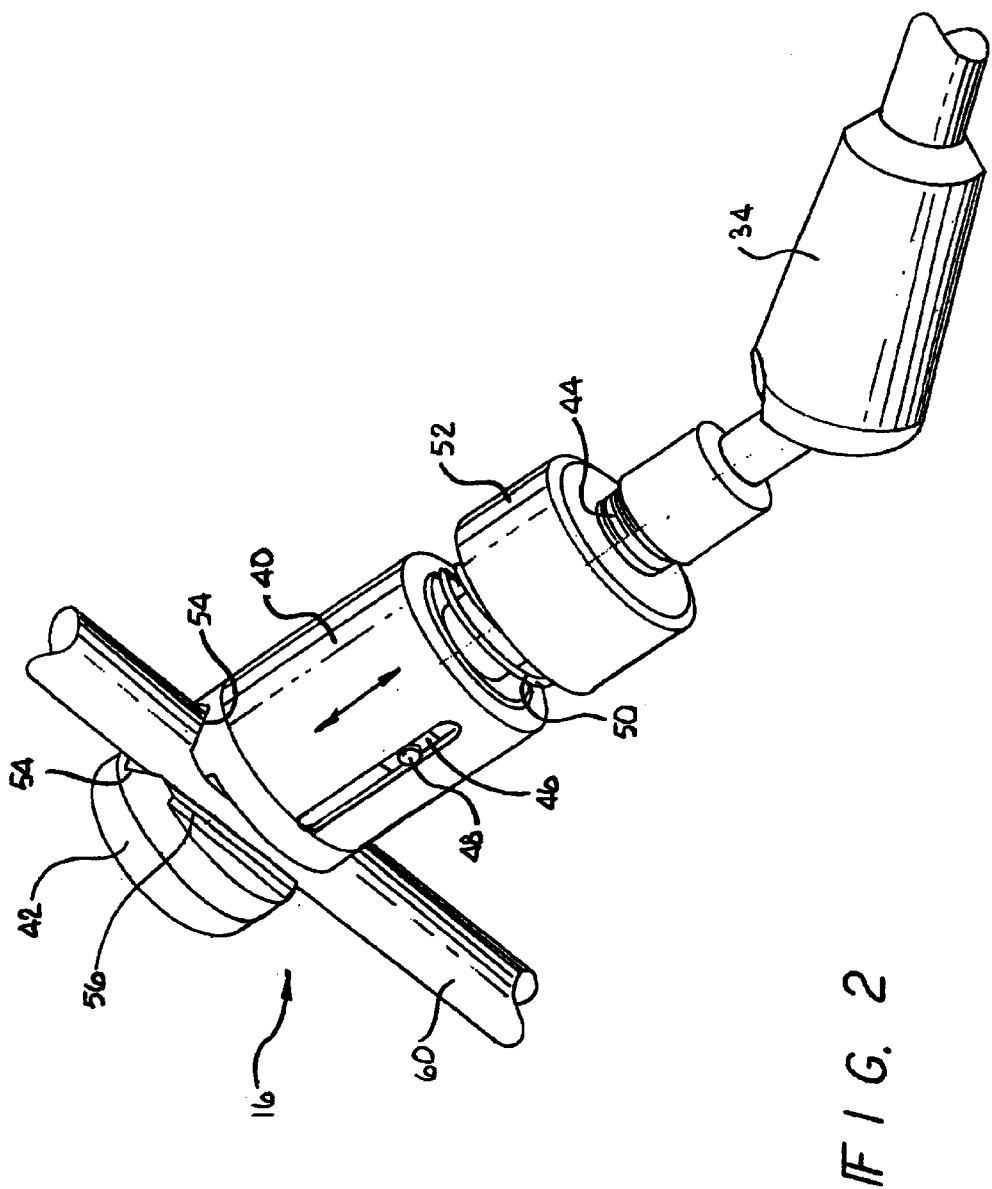
FIG. 2 is an enlarged view of an end effector of the support arm.

FIG. 2 shows an embodiment of the end effector 16. The end effector 16 includes a retractable jaw member 40 that can move relative to a stationary jaw member 42 along an internal threaded shaft 44. Movement of the retractable jaw member 40 may be guided by an internal bearing collar 46 that is attached to the shaft 44 by a pin 48. The retractable jaw member 40 may be biased into a closed position by a spring 50. The deflection and resultant spring force of the spring 50 may be varied by rotating an adjustment collar 52 that can be moved along the shaft 44.

The jaws 40 and 42 may have channels 54 that accommodate cylindrical shaped instruments such as a heart stabilizer 60. The channels 54 may have two different radiuses to accommodate instruments having different diameters. By way of example, the channels 54 may receive instrument shafts having diameters that range between 2 and 15 millimeters. The jaws 40 and 42 may also have end plates 56 that accommodate rectangular shaped instruments.

Figure 3:
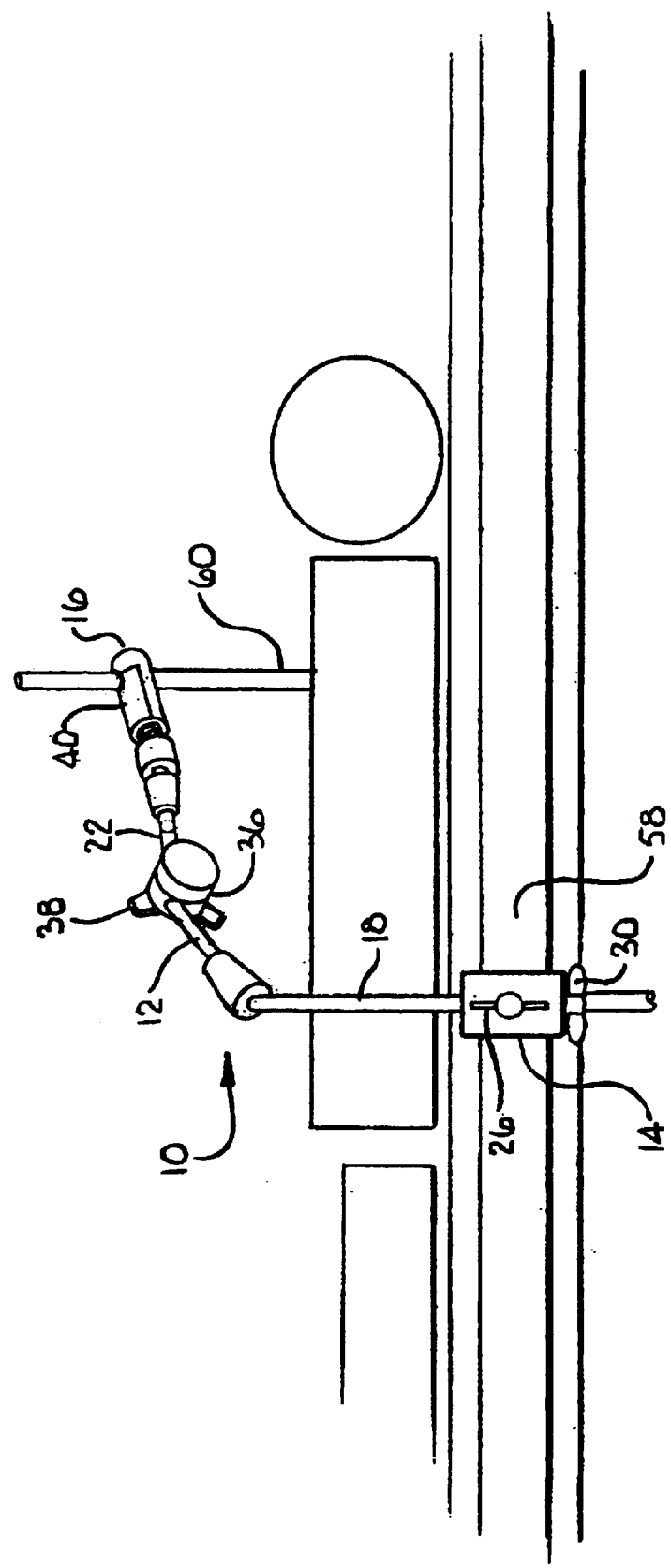
FIG. 3 is a perspective view of the support arm coupled to a table and a heart stabilizer coupled to an end effector of the arm.

As shown in FIG. 3, the table mount 14 can be mounted to a table rail 58. A surgical instrument 60 such as a heart stabilizer is typically inserted into a patient to perform a surgical procedure. The position of the end effector 16 is aligned with the surgical instrument 60 by adjusting the arm 12. The surgical instrument 60 is then attached to the end effector 16 by retracting and then releasing the retractable jaw member 40. The arm 12 is locked in place by rotating the locking knob 38. A surgeon can both hold and secure the instrument 60 to the support arm 10. Alternatively, the surgeon can hold the surgical instrument 60 and another person can couple the instrument 60 to the end effector 16. The support arm 10 will hold the instrument 60 during a surgical procedure without requiring any additional personnel to hold the instrument 60. The surgical instrument 60 can be released by retracting the jaw member 40 and pulling the instrument 60 away from the support arm 10.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the at art.

What is claimed is:

1. A support arm assembly, comprising:
   a table mount;
   an arm coupled to said table mount;
   an end effector coupled to said arm, said end effector having a stationary jaw member, a retractable jaw member biased to move toward the stationary jaw member; and
   a heart stabilizer having a shaft, the shaft held between the retractable jaw member and the stationary jaw member without rotation of a threaded fastener.

2. The support arm of claim 1, wherein said arm is adjustable and includes a locking knob which locks the arm in a fixed position.

3. The support arm of claim 1, wherein said table mount includes a jaw and a table knob.

4. The support arm of claim 1, wherein said arm includes a first linkage, a second linkage coupled to said first linkage, and a third linkage coupled to said second linkage and said end effector.

5. The support arm of claim 4, wherein said first linkage is adapted to move relative to said table mount.

6. The support arm of claim 4, wherein said second linkage can move relative to said first linkage, said third linkage can move relative to said second linkage and said end effector can move relative to said third linkage.

7. The support arm of claim 1, wherein said end effector includes a channel that receives the shaft of the heart stabilizer.

8. The support arm of claim 1, wherein said end effector includes a plate.

9. A support arm assembly, comprising:
   a table mount adapted to be secured to the table;
   a first linkage coupled to said table mount;
   a second linkage pivotally coupled to said first linkage;
   a third linkage pivotally coupled to said second linkage;
   an end effector pivotally coupled to said third linkage, the end effector having a stationary jaw member, a retractable jaw member biased to move relative to the stationary jaw member; and
   a heart stabilizer having a shaft, the shaft held between the retractable jaw member and the stationary jaw member without rotation of at fastener.

10. The support am of claim 9, further comprising a locking knob that can be manipulated to lock said first, second and third linkage arms.

11. The support arm of claim 9, wherein said table mount includes a jaw and a table knob.

12. A method for coupling a heart stabilizer to a table, comprising:
    mounting a support arm to the table;
    adjusting a position of an end effector of the support arm, the end effector having a retractable jaw member;
    retracting the jaw member, the retraction creates a spring force;
    inserting a heart stabilizer into the end effector; and
    releasing the jaw member so that the spring force returns the jaw member and secures the end effector to the heart stabilizer.

13. The method of claim 12, wherein a first person holds the heart stabilizer while a second person couples the heart stabilizer to the end effector.

14. The method of claim 12, wherein adjusting the position of the end effector of the support arm, retracting the jaw member and releasing the jaw member is performed by one hand of a user while the inserting of the heart stabilizer into the end effector is performed by another hand of the user.

15. The method of claim 12, further comprising locking the adjusted support arm into an operating position.

16. The method of claim 12, further comprising positioning a patient on the table, positioning the heart stabilizer in relation to a heart of the patient prior to the inserting step, and maintaining the position of the heart stabilizer during the inserting step.

17. The method of claim 16, wherein the adjusting step is performed aft positioning the heart stabilizer.

18. The method of claim 12, wherein the end effector includes a stationary jaw member, the heart stabilizer includes a shaft and the inserting step comprises inserting the shaft between the retractable jaw member and the stationary jaw member.

19. The support arm of claim 7, wherein the channel is sized to receive shafts having diameters in a range between 2 and 15 millimeters.

20. The support arm of claim 7, wherein the channel is shaped to receive cylindrical shaped shafts.

21. The support arm of claim 7, wherein the channel is shaped to receive square shaped shafts.

22. The support arm of claim 1, wherein said biased retractable jaw member moves relative to the stationary jaw member by action of a spring.

23. The support arm of claim 9, wherein said biased retractable jaw member moves relative to the stationary jaw member by action of a spring.

* * * * *